(12) United States Patent
Cavin et al.

(10) Patent No.: US 10,426,338 B2
(45) Date of Patent: Oct. 1, 2019

(54) SCLERAL COIL EYE TRACKING SYSTEM

(71) Applicant: Facebook Technologies, LLC, Menlo Park, CA (US)

(72) Inventors: Robert Dale Cavin, Kirkland, WA (US); Eric Michael Whitmire, Redmond, WA (US); Brian Michael Scally, Seattle, WA (US); Laura Cristina Trutoiu, Seattle, WA (US)

(73) Assignee: Facebook Technologies, LLC, Menlo Park, CA (US)

( * ) Notice: Subject to any disclaimer, the term of this patent is extended or adjusted under 35 U.S.C. 154(b) by 488 days.

(21) Appl. No.: 15/381,896

(22) Filed: Dec. 16, 2016

(65) Prior Publication Data

US 2017/0172409 A1   Jun. 22, 2017

Related U.S. Application Data

(60) Provisional application No. 62/271,022, filed on Dec. 22, 2015.

(51) Int. Cl.
*A61B 3/113* (2006.01)
*A61B 5/04* (2006.01)
*A61B 5/00* (2006.01)

(52) U.S. Cl.
CPC .......... *A61B 3/113* (2013.01); *A61B 5/04005* (2013.01); *A61B 5/6803* (2013.01); *A61B 5/7445* (2013.01); *A61B 2562/0223* (2013.01)

(58) Field of Classification Search
CPC ..... A61B 3/0025; A61B 3/103; A61B 3/1015; A61B 3/14; A61B 3/10
USPC ................................. 351/205, 209, 212, 237
See application file for complete search history.

(56) References Cited

PUBLICATIONS

U.S. Appl. No. 14/589,755, filed Jan. 5, 2015, Inventors: Dov Katz et al.
U.S. Appl. No. 14/946,143, filed Nov. 19, 2015, Inventors: Volga Aksoy et al.

*Primary Examiner* — Mohammed A Hasan
(74) *Attorney, Agent, or Firm* — Fenwick & West, LLP

(57) ABSTRACT

A wearable eye tracking system includes a pair of looping coils in a Helmholtz configuration and an additional looping coil. In one configuration, areas enclosed by the pair of looping coils in the Helmholtz configuration are in parallel with each other, while an area enclosed by the additional looping coil is offset from (i.e., not parallel with) the areas enclosed by the pair of looping coils. In this configuration, the pair of looping coils generates uniform magnetic fields between the two areas of the pair of looping coils in a first direction orthogonal to the areas of the pair of looping coils, and the additional looping coil generates additional non-uniform (or divergent) magnetic fields in a second direction transversal to the first direction.

20 Claims, 7 Drawing Sheets

SCLERAL COIL EYE TRACKING SYSTEM

CROSS REFERENCE TO RELATED APPLICATION

This application claims priority to and the benefit of U.S. Provisional Patent Application No. 62/271,022 filed on Dec. 22, 2015, which is incorporated by reference in its entirety.

BACKGROUND

The present disclosure generally relates to scleral eye tracking, and specifically, to scleral coil eye tracking on head mounted displays.

Scleral search coil (SSC) tracking is one technique for performing eye tracking that is both fast and accurate. One example SSC tracking system can perform eye tracking with a resolution of 0.002 degree with a relatively high sampling frequency (e.g., 8 kHz), where an optical tracking system can perform eye tracking at a lower sampling frequency (e.g., 300 Hz). Large generator coils create a uniform magnetic field across a subject's head. The subject wears, e.g., contact lenses including scleral coils. For a given eye, of the subject, depending on an orientation of the eye, the field induces a signal (e.g., a voltage or current) in the scleral coil. By examining the magnitude of the signal in the scleral coil, it is possible to estimate the orientation of the eye. But conventional SSC tracking systems are not ideal for eye tracking in systems like, e.g., head-mounted displays in virtual reality and/or augmented reality systems, where small form factor and freedom of movement are desired. In conventional SSC tracking systems, the accuracy of the estimation of the orientation of the eye scales with a size of the generator coils. For example, to obtain an accurate estimation of the orientation of the user eye, the generator coils (e.g., several meters in diameter) entirely surround the subject, and thus are inefficient for space limited systems. Moreover, the subject's head is maintained in a fixed position for estimating the orientation of the eye, thereby restricting the user's head movement.

SUMMARY

A wearable eye tracking system includes a pair of looping coils in a Helmholtz configuration and an additional looping coil. In one configuration, areas enclosed by the pair of looping coils in the Helmholtz configuration are in parallel with each other, while an area enclosed by the additional looping coil is offset from (i.e., not parallel with) the areas enclosed by the pair of looping coils. In this configuration, the pair of looping coils generates uniform magnetic fields between the two areas of the pair of looping coils in a first direction orthogonal to the areas of the pair of looping coils, and the additional looping coil generates additional non-uniform (or divergent) magnetic fields in a second direction transversal to the first direction.

In some embodiments, a head-mounted display is coupled to a pair of looping coils in a Helmholtz confirmation and an additional looping coil, such that the HMD is situated between the pair of looping coils. A user of the HMD wears a scleral lens on an eye of the user. Magnetic fields generated by the pair of looping coils and the additional looping coil induce electric signals at the scleral lens, according to an orientation of an eye of the user. The scleral lens includes a torsional coil comprising two half loops, where the two half loops of the torsional coil render two different measurements of electric signals per magnetic fields according to an orientation of the user eye. In one aspect, electric signals induced by the uniform magnetic fields at the torsional coil allow an estimation of the orientation of the eye. Electric signals induced by the additional magnetic fields at the torsional coil provide an additional degree of freedom, and enhance the accuracy of the estimation of the orientation of the eye, than electric signals induced without the additional magnetic fields. Hence, the eye tracking system can be implemented in a portable form factor wearable by a user.

DETAILED DESCRIPTION

Example Eye Tracking System

Figure 1A:
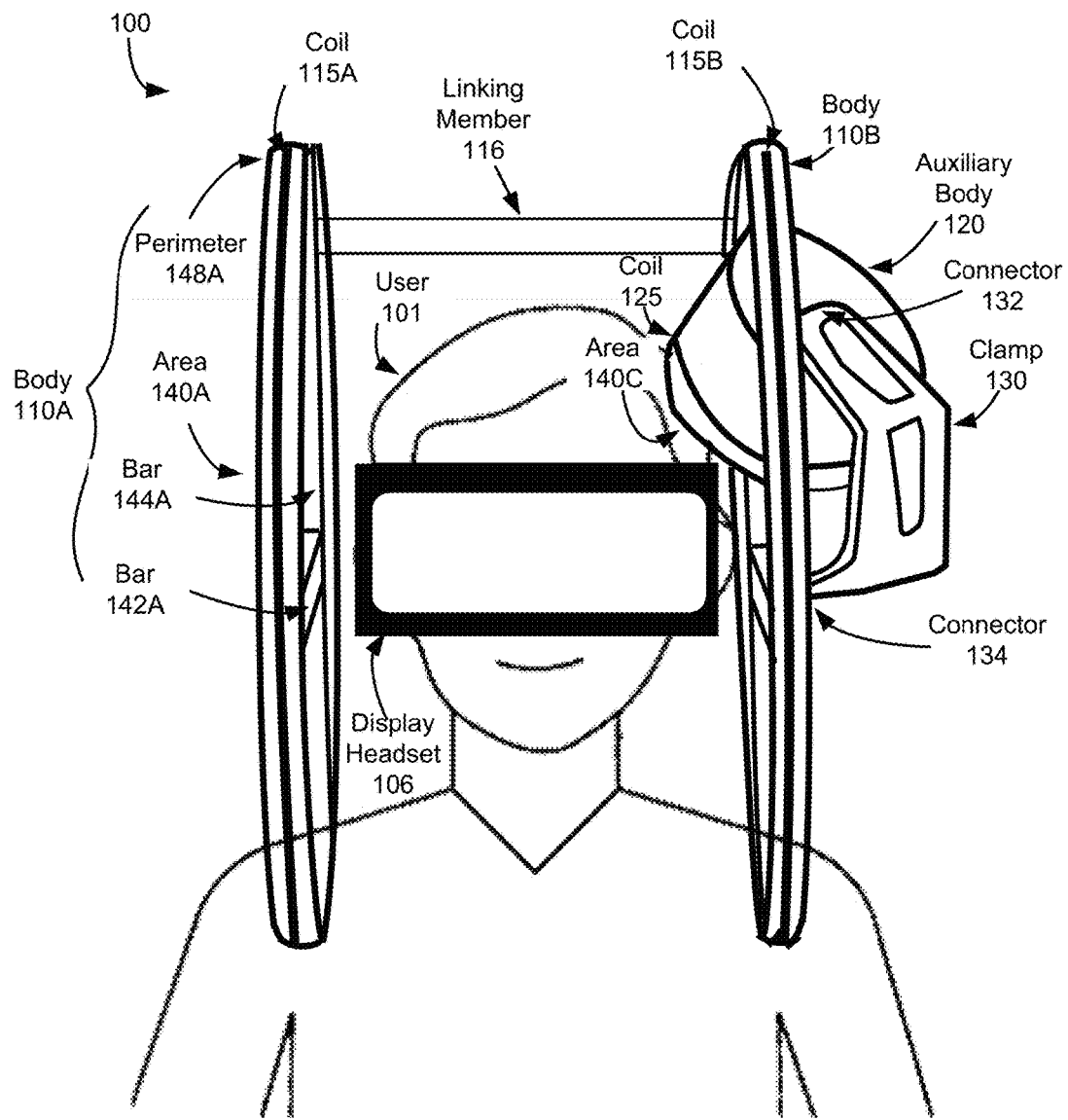
FIG. 1A is a front view of a scleral eye tracking system, in accordance with an embodiment.

FIG. 1A is a front view of a scleral eye tracking system 100, in accordance with an embodiment. The user 101 wears scleral lenses (not show in FIG. 1A), and a display headset 106 that may be a virtual reality (VR) headset or an augmented reality (AR) headset for presenting an image of a VR or an AR to the user 101. In one embodiment, the display headset 106 is coupled to the scleral eye tracking system 100, which tracks orientations of eyes of the user 101 while an image is presented on the display headset 106. The scleral eye tracking system 100 generates magnetic fields toward user eyes or the display headset 106. The magnetic fields generated by the scleral eye tracking system 100 induce electric signals (e.g., voltage or current) at the scleral lenses according to the orientations of the eyes. Hence, the orientations of the eyes can be estimated according to the electric signals induced by the magnetic fields from the scleral eye tracking system 100.

In one embodiment, the scleral eye tracking system 100 includes a first coil 115A, a second coil 115B, and an additional coil 125 configured to generate magnetic fields toward the user eye or the display headset 106. The coils 115 and 125 are conductive coils (e.g., copper, aluminum, etc.), and applied with two different AC currents for generating magnetic fields, as described in detail with respect to FIG. 2. The scleral eye tracking system 100 further includes bodies 110A, 110B, a linking member 116, an auxiliary body 120, a clamp 130, and connectors 132 and 134. The coil 115A is wound on a perimeter of the body 110A; the coil 115B is wound on a perimeter of the body 110B; and the additional coil 125 is wound on a perimeter of the auxiliary body 120. The coils 115A and 115B can be wound in a same direction or in an opposite direction. The bodies 110A, 110B and the auxiliary body 120 are coupled to each other through the linking member 116, the connector 134, the clamp 130 and the connector 132. In one implementation, the bodies 110A, 110B, and the auxiliary body 120 are fabricated through a three dimensional printing technology with a digital ABS plastic. Between the bodies 110A and 110B, the display headset 106 can be mounted on at least one of the bodies 110A and 110B through a mount (not shown in FIG. 1A). In other embodiments, the scleral eye tracking system 100 includes more, less, or different components than shown in FIG. 1A. For example, there may be multiple linking members 116 between the bodies 110A and 110B. In one embodiment, the scleral eye tracking system 100 with the auxiliary body 120 and the additional coil 125 is for tracking a single eye. In other embodiments, another auxiliary body with an additional coil (not shown) is added for tracking two eyes.

The body 110A is a component on which the coil 115A can be wound. In one embodiment, the body 110A includes an area 140A facing a first side of the display headset 106, and a perimeter 148A enclosing the area 140A. The perimeter 148A is made of a solid material (e.g., plastic or a metal), on which the coil 115A can be wound. The area 140A enclosed by the perimeter 148A can be an air gap or filled with ferrite materials to improve magnetic field strength. Examples of shapes of the area 140A of the body 110A include circular, oval, rectangular, and polygonal shape. In the example illustrated in FIG. 1A, the body 110A (and the body 110B) has a diameter of 36 cm. In the embodiment shown in FIG. 1A, the body 110A includes bars 144A and 142A on which the display headset 106 can be coupled to. The bars 142A and 144A may be made of the same material as the perimeter 148A, or may be made of different materials. The bar 142A extends within the area 140A in a direction from a portion of the perimeter 148A, and the bar 144A extends within the area 140A in another direction from another portion of the perimeter 148A. Preferably, the display headset 106 is coupled to an intersection of the bars 144A and 142A through a mount (not shown in FIG. 1A), generally located at a center of the area 140A. In other embodiments, the bars 142A and 144A can be omitted.

The body 110B is a component on which the coil 115B can be wound. The body 110B includes a similar structure as the body 110A, except the area 140B (not shown in FIG. 1A for simplicity but shown in FIG. 1B) of the body 110B facing the area 140A of the body 110A in parallel is coupled to the second side of the display headset 106. Therefore, the detailed description thereof is omitted herein for the sake of brevity.

The linking member 116 is a connecting component between the bodies 110A and 110B. In one embodiment, the linking member 116 is coupled to the perimeters 148 of the bodies 110. In other embodiments, the linking member 116 is coupled to one or more of the bars 142, and the bars 144. In one example, the linking member 116 is located above the display headset 106, but may be located anywhere between the bodies 110 with respect to the display headset 106. The linking member 116 can be made of the same material as the perimeter 148 or the bars 142, 144. The linking member 116 is elongated in a direction orthogonal to the parallel areas 140A and 140B of the bodies 110. Alternatively, the linking member 116 can be elongated in any direction.

The auxiliary body 120 is a component on which the coil 125 can be wound. The auxiliary body 120 includes a similar structure as the body 110A or 110B, except the area 140C of the auxiliary body 120 enclosed by a perimeter (not shown in FIG. 1A) of the auxiliary body 120 faces the display headset 106 in a direction different from an orthogonal direction of the parallel areas 140A and 140B. Hence, the area 140C of the auxiliary body 120 is offset from the bodies 110A and 110B. In addition, the auxiliary body 120 is smaller than the bodies 110A and 110B, such that the area 140C of the auxiliary body 120 is smaller than the parallel areas 140A and 140B. In the example illustrated in FIG. 1A, the body 110C has a diameter of 10 cm. In the embodiment illustrated in FIG. 1A, the auxiliary body 120 is coupled to the body 110B. Alternatively, the auxiliary body 120 can be coupled to the body 110A instead. In another embodiment, another auxiliary body with a coil wound on said another auxiliary body may be coupled to the body 110A, while the auxiliary body 120 with the coil 125 is coupled to the body 110B. In the embodiment with said another auxiliary body, the coil wound on said another auxiliary body generates a non-uniform field for performing eye tracking for one eye, where the coil 125 wound on the auxiliary body 120 generates a non-uniform field for performing eye tracking for the other eye.

The clamp 130 is a component through which the auxiliary body 120 and the body 110B can be coupled. In one implementation, the clamp 130 is bent such that the area of the auxiliary body 120 can face the display headset 106. The clamp 130 can be made of the same material of the body 110B or the bars 144. One end of the clamp 130 is coupled to the body 110B (e.g., bar 142B shown in FIG. 1B) through the connector 134 and another end of the clamp 130 is coupled to the auxiliary body 120 through the connector 132. The connectors 132 and 134 can be screws enabling the clamp 130 and the auxiliary body 120 to swivel for changing a direction of the auxiliary body 120. Alternatively, the connectors 132 and 134 secure the auxiliary body 120 and the clamp 130 in a fixed position.

Figure 1B:
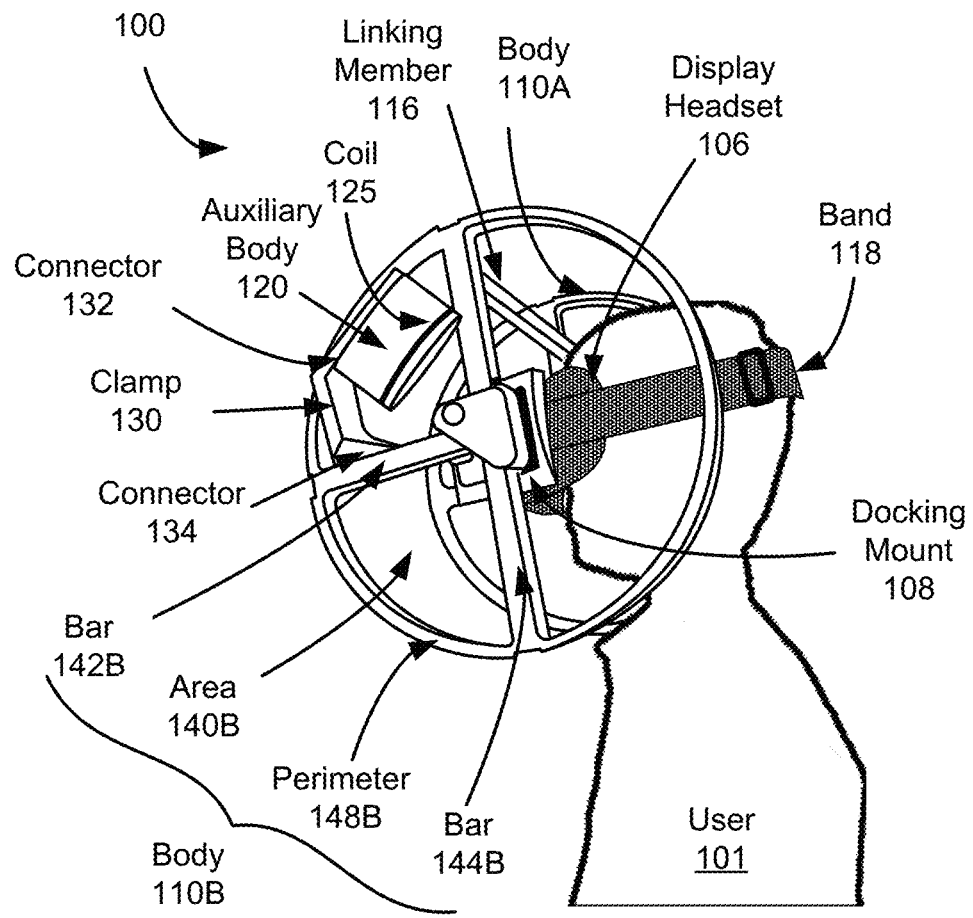
FIG. 1B is a side view of the scleral eye tracking system of FIG. 1A, in accordance with an embodiment.

FIG. 1B is a side view of the scleral eye tracking system 100 of FIG. 1A, in accordance with an embodiment. The scleral eye tracking system 100 on a left side of the user 101 is shown in FIG. 1B, exposing the area 140B of the body 110B. The body 110A is coupled to the body 110B through the linking member 116 above the display headset 106, where a portion of the body 110A is hidden by the user 101. The display headset 106 can be secured on a head of the user 101 through the band 118, and also can be coupled between the bodies 110A and 110B through a docking mount 108 as described below.

In the example shown in FIG. 1B, the body 110B includes the area 140B of a circular shape, and the perimeter 148B circumscribing the area 140B. The body 110B further includes the bar 144B extending from a first portion of the perimeter 148B to a second portion of the perimeter 148B in a direction, and the bar 142B extending from a third portion of the perimeter 148B in another direction. Preferably, the bar 142 extends from the third portion of the perimeter 148B to a center of the bar 144B, which is also the center of the area 140B.

A docking mount 108 is a component configured to couple the display headset 106 to the body 110. In one embodiment, the docking mount 108 is coupled to the center of the area 140B of the body 110B at the intersection of the bars 142B and 144B. Moreover, the docking mount 108 is configured to receive a side of the display headset, and secures the side of the display headset 106 to the body 110B. The docking mount 108 can be a mechanical component such as a latch, screws, a hook and loop type fastener (e.g., Velcro®), or any component for affixing the docking mount 108 to the body 110.

The body 110A includes a similar structure of the body 110B except another docking mount 108 is coupled to a center of the area of the body 110A for securing another side (e.g., right side) of the display headset 106 to the body 110A, therefore the detailed description is omitted herein for the simplicity.

The auxiliary body 120 is coupled to the body 110B through the clamp 130. In the example shown in FIG. 1B, a bottom end of the clamp 130 is coupled to the bar 142B through the connector 134 and a top end of the clamp 130 is coupled to the auxiliary body 120 through the connector 132. Alternatively, the auxiliary body 120 may be coupled to the linking member 116, the bar 144B or the perimeter 148B.

Figure 2:
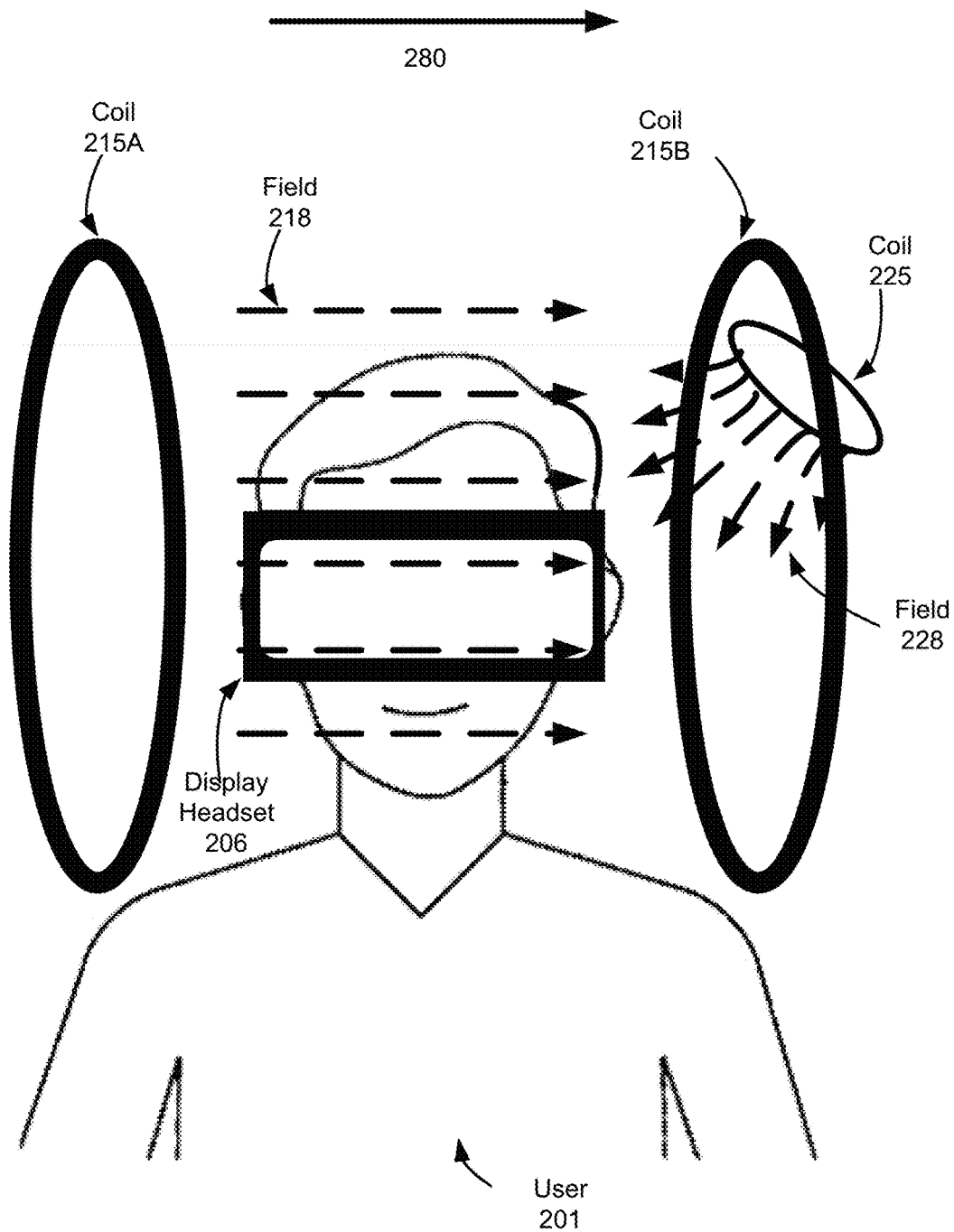
FIG. 2 illustrates example magnetic fields generated by a scleral eye tracking system, in accordance with an embodiment.

FIG. 2 illustrates example magnetic fields 218 and 228 generated by the scleral eye tracking system, in accordance with an embodiment. The magnetic field 218 is generated between coils 215A and 215B and is substantially uniform in direction and magnitude at the location corresponding to user eyes or the display headset 106. Additionally, the magnetic field 228 is generated by the coil 225, and may be non-uniform (or divergent). A display headset 206 is placed between the coils 215A and 215B, where one side of the display headset 206 faces an area enclosed by the coil 215A, and another side of the display headset 206 faces an area enclosed by the coil 215B. The coils 215A, 215B, and 225 are applied with corresponding AC currents to generate the magnetic fields 218 and 228 through the display headset 206, while an image is presented to a user 201 on the display headset 206. Each of the coils 215A, 215B, and 225 may be coupled to a corresponding capacitor bank or a varactor to tune the resonance frequencies of the coils. In some embodiments, the coils 215A and 215B may be e.g., the coils 115A and 115B of FIG. 1A; the coil 225 may be e.g., the coil 125 of FIG. 1A; and the display headset 206 may be e.g., the display headset 106 of FIG. 1A. In one embodiment, the coils 215A and 215B are configured in a Helmholtz configuration and applied with AC currents at a first frequency (e.g., between 10 kHz and 100 kHz) and a first amplitude (e.g., 1 A) to induce the magnetic field 218 between the coils 215A and 215B in a direction 280 perpendicular to the parallel areas enclosed by the coils 215A and 215B. In case the coils 215A and 215B are wound in the same direction, AC currents applied to the coils 215A and 215B have a same phase. Alternatively, in case the coils 215A and 215B are wound in directions opposite to each other, AC currents applied to the coils 215A and 215B have opposite phases with each other. Moreover, the coil 225 is applied with another AC current at a second frequency (e.g., between 10 kHz and 100 kHz) different from the first frequency and a second amplitude (e.g., 1 A) to induce non-uniform (e.g., divergent) magnetic field 228.

Figure 3A:
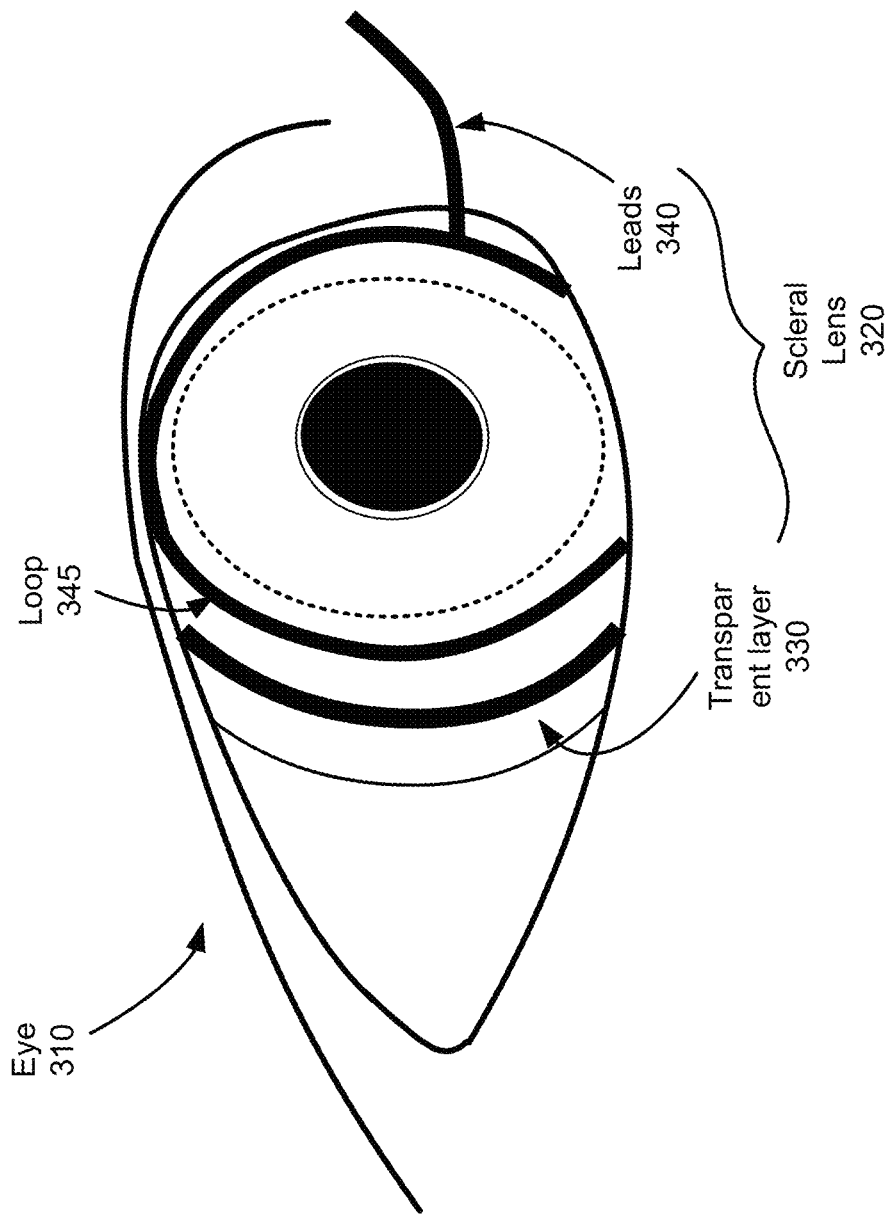
FIG. 3A is a perspective view of a scleral lens on a user eye for performing scleral eye tracking, in accordance with an embodiment.

FIG. 3A is a perspective view of a scleral lens 320 on a user eye 310 for performing scleral eye tracking, in accordance with an embodiment. The scleral lens 320 includes a transparent layer 330 and conductive leads 340. A surface of the transparent layer 330 is coupled to a pupil of the eye 310, and another surface of the transparent layer 330 away from the pupil of the eye 310 is coupled to a portion of the leads 340. The portion of the leads 340 is coupled to a portion the transparent layer 330 corresponding to a portion of a sclera of the eye 310, and may be wound to form one or more loops 345 on the other surface of the transparent layer 330. Thus, the user's view is not obscured by the leads 340. Ends of the leads 340 may be extended away from the transparent layer 330 and electrically coupled to a sensing system (not shown) for sensing electric signals (e.g., voltage or current) at the leads 340. The electric signals can be induced at the leads 340 by magnetic fields through the one or more loops 345. An amplitude and phase of magnetic fields passing through the one or more loops 345 vary, according to a position of the leads 340. Hence, the electric signals induced at the leads 340 vary according to an orientation of the eye 310. Therefore, an orientation of the eye 310 can be estimated based on the electric signals induced at the leads 340 and sensed through the ends of the leads 340.

In one aspect, the user wears the scleral lens 320 and a display headset (e.g., display headset 106 of FIG. 1A) coupled to a scleral eye tracking system (e.g., scleral eye tracking system 100 of FIG. 1A). When an image is presented to the user on the display headset 106, the scleral eye tracking system 100 generates magnetic fields (e.g., magnetic fields 218 and 228 of FIG. 2). Moreover, how a human vestibular-ocular system responds to an image of e.g., a virtual reality or an augmented reality can be studied by analyzing the electric signals induced at the leads 340 with respect to the image presented at the display headset.

In the embodiment in which uniform magnetic fields 218 are induced by supplying a first current at a first frequency and first amplitude to the coils 215A and 215B of FIG. 2 and non-uniform magnetic fields 228 are induced by supplying a second current at a second frequency and second amplitude to the coil 225 of FIG. 2, electric signals induced by the magnetic fields 218 and 228 contain two frequency components corresponding to the first frequency and the second frequency. By filtering the electric signals in a frequency domain, two measurements of the electric signals corresponding to the magnetic fields 218 and 228 can be obtained through the leads 340.

Figure 3B:
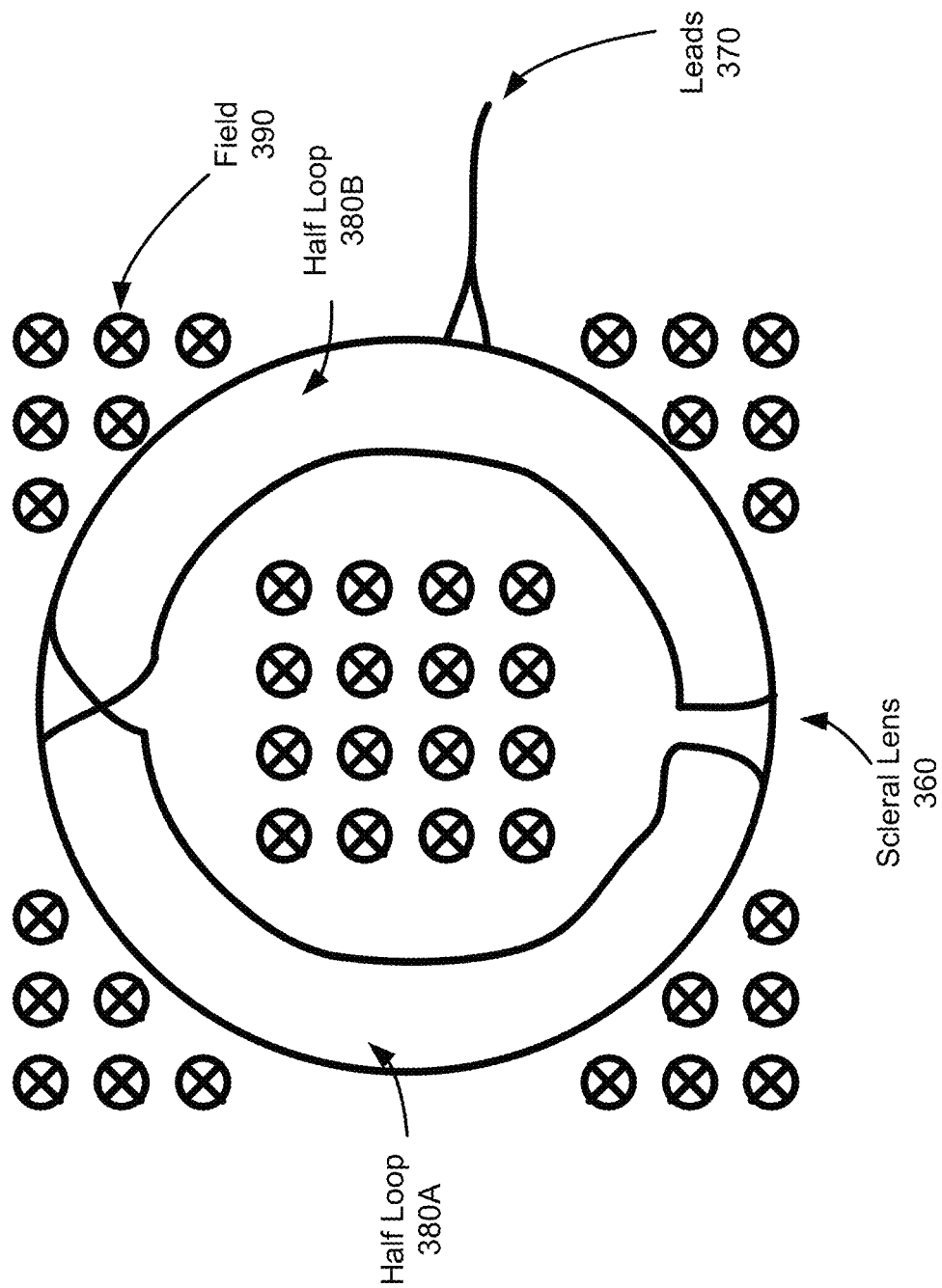
FIG. 3B is an example scleral lens of FIG. 3A, and magnetic fields through the scleral lens, in accordance with an embodiment.

FIG. 3B is an example scleral lens 360 of FIG. 3A, and magnetic fields 390 through the scleral lens 360, in accordance with an embodiment. The scleral lens 360 includes leads 370 forming a torsional coil comprising two half loops 380A and 380B. The magnetic fields 390 through the half loops 380A and 380B can induce electric signals at the lead 370. In some embodiments, the scleral lens 360 may be e.g., the scleral lens 320 of FIG. 3A; the lead 370 may be e.g., the lead 340 of FIG. 3A; half loops 380A and 380B of the scleral lens 360 may be e.g., one or more loops 345 of FIG. 3A; and the magnetic fields 390 may be e.g., the magnetic fields 218 and 228 of FIG. 2. The two half loops 380A and 380B are formed on a portion of a transparent layer (not shown in FIG. 3B) of the scleral lens 360 corresponding to sclera of an eye.

In one embodiment, the magnetic fields 390 through the two half loops 380A and 380B induce corresponding electric signals. By use of the torsional coil including the two half loops 380A, 380B, two different measurements of electric signals in response to a same magnetic field can be obtained, thereby increasing a measurement efficiency of electric signals in response to the magnetic fields 390 for a given area compared to a solenoid coil through which a single measurement of a single magnetic field can be obtained. In case the uniform magnetic fields 218 and the non-uniform (or divergent) magnetic fields 228 are applied to the torsional coil, four measurements of the electric signals in response to the two magnetic fields 218 and 228 can be obtained. Accordingly, accuracy of the eye tracking can be improved, enabling the scleral eye tracking system 100 to be implemented in a portable form factor.

In one embodiment, a field divergence model is obtained to determine an eye orientation. The field divergence model accounts for any divergence (i.e., non-uniformity) of magnetic fields 218 and 228, and maps measured magnetic field to an ideal uniform magnetic field according to an eye orientation. Any errors (or divergence) in the magnetic fields from the coils 215A, 215B, and 225 can reduce accuracy in determining the eye orientation. Thus, by use of the field divergence model, measured signal due to fields 218 and 228 incorporating any non-uniformity can be converted into a signal without any divergence, then the converted signal can be used for determining an eye orientation.

In one aspect, the field divergence model is obtained through a bootstrapping approach. A difficulty in obtaining the field divergence model is that errors in the measurement due to the non-uniformity of the fields depend on an eye orientation. Thus, accurate field divergence model cannot be obtained without the accurate eye orientation, but the accurate eye orientation cannot be obtained without the field divergence model. Such quandary can be resolved through a bootstrapping approach. In one example, a rough estimation of an eye orientation can be obtained, and the estimation is used to obtain the field divergence model.

Figure 4:
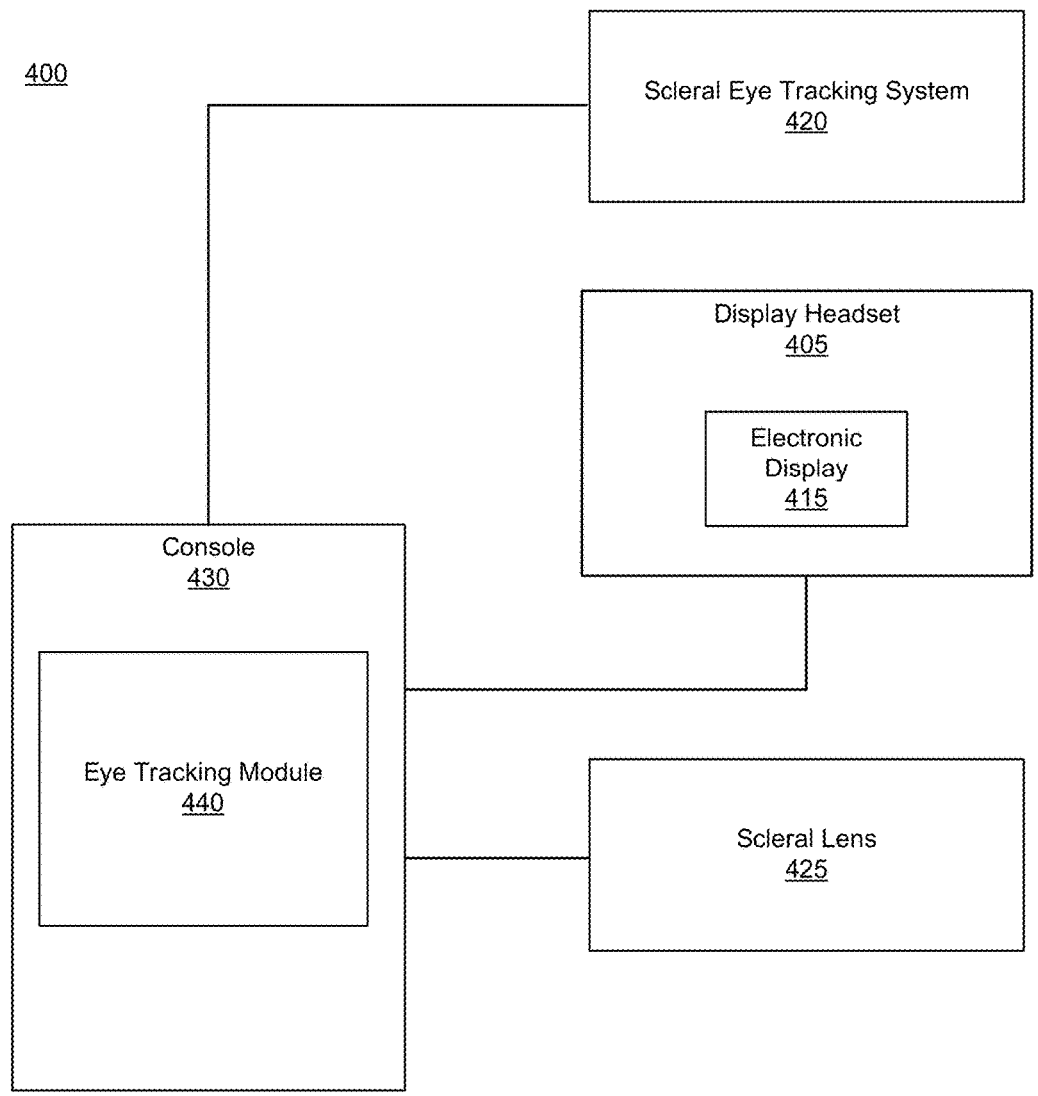
FIG. 4 is a block diagram of a system environment for performing scleral eye tracking in a head-mounted display, in accordance with an embodiment.

FIG. 4 is a block diagram of a system environment 400 for performing scleral eye tracking in a head-mounted display (HMD) 405, in accordance with an embodiment. The system environment 400 shown by FIG. 4 comprises the HMD 405 (also referred to as a display headset 405), a scleral eye tracking system 420, a scleral lens 425, and a console 430. While FIG. 4 shows an example system environment 400 including one display headset 405, one scleral eye tracking system 420, one scleral lens 425, and one console 430, in other embodiments any number of these components may be included in the system environment 400. For example, there may be multiple display headsets 405, multiple scleral eye tracking systems 420, and multiple scleral lenses 425. In alternative configurations, different and/or additional components may be included in the system environment 400. Similarly, the functions can be distributed among the components in a different manner than is described here. For example, some or all of the functionality of the console 430 may be contained within the display headset 405.

The system environment 400 is part of a virtual reality (VR) and/or augmented reality (AR) environment. For simplicity, components relating to generation of the VR and/or AR environment are omitted from discussion. Details of a system environment for generating a VR and/or AR system environment are further described in U.S. patent application Ser. No. 14/589,755, filed on May 26, 2015 and U.S. patent application Ser. No. 14/946,143, filed on Nov. 19, 2015, each of which is hereby incorporated by reference in its entirety.

The display headset 405 is a head-mounted display that presents media to a user wearing the display headset 405. In some embodiments, the display headset 405 may be e.g., the display headset 106 of FIG. 1A. Examples of media presented by the display headset 405 include one or more images, video, audio, or any combination thereof for presenting virtual reality or augmented reality. The display headset 405 includes an electronic display 415 that displays images to the user in accordance with data received from the console 430. Examples of the electronic display 415 include a liquid crystal display device, organic light emitting diode display device, or any flat screen display device.

The scleral eye tracking system 420 generates magnetic fields through the display headset 405. The display headset is worn by a user who is wearing a scleral lens 425 on one or both of their eyes. The magnetic fields cause the one or more scleral lenses 425 to generate electric signals (e.g., electric signals may be induced currents) that are output to the console 430. The scleral eye tracking system 420 is an embodiment of the scleral eye tracking system 100, and the scleral lens 425 is an embodiment of the scleral lens 360. Thus, the detailed descriptions thereof are omitted herein.

The console 430 provides content to the display headset 405 for presentation to the user. In the example shown in FIG. 4, the console 430 includes an eye tracking module 440. Some embodiments of the console 430 have different modules than those described in conjunction with FIG. 4. Similarly, the functions further described below may be distributed among components of the console 430 in a different manner than is described here.

The eye tracking module 440 calibrates the scleral eye tracking system 420. The eye tracking module 440 generates an indicator for each coordinate of a set of coordinates in a virtual space that may be presented via the display headset 405. The set of coordinates of the electronic display 415 corresponds to a set of ground truth values for different eye orientations. The eye tracking module 440 supplies or causes a current supply unit (not shown in FIG. 4) to supply AC currents to the scleral eye tracking system 420 for generating magnetic fields. While the magnetic fields (e.g., by the Helmholtz pair and the offset coil) are generated by the scleral eye tracking system 420, the eye tracking module 440 instructs the display headset 405 to display an indicator, of the set of indicators, and prompts the user to look at the displayed indicator. An eye looking at the displayed indicator has a specific orientation. For each, scleral lens 425, specific electric signals are generated by the magnetic fields, the specific electric signals correspond to an eye orientation of the eye coupled to the scleral lens 425. The eye tracking module 440 maps the electric signals to the eye orientation associated with the displayed indicator. The eye tracking module 440 then moves on to a different indicator in the set of indicators, and repeats mapping electric signals from the one or more scleral lenses 425 with an eye orientation associated with the different indicator. The indicator can be presented as a bright dot (e.g., blue, green, or red) or a crosshair presented on the electronic display 415. In one example, a display area of the electronic display 415 may be divided into a predetermined number of regions (e.g., 25), and the indicator is displayed at a center of each region at a time. The indicator may be presented at a coordinate of the set of coordinates for a predetermined duration (e.g., 5 seconds), and presented at a next coordinate of the set of coordinates.

After a threshold number of indicators have been displayed and their corresponding induced current (or voltage) values in the one or more scleral lenses 425 have been mapped to corresponding eye orientations, the eye tracking module 440 interpolates mapped data (i.e., the mapping between the different electric signals to different eye orientations) to generate a field divergence model. In some embodiments, the threshold number may be the number of indicators in the set of indicators. However, in other embodiments, it may be a fewer number. Regardless, the size of the threshold number correlates with performance of the field divergence model. For example, a threshold number of 25 results in an error of 0.43 degree difference between actual and estimated eye orientation. As the threshold number is reduced, the error increases, for example, a threshold number of 5, results in a 1 degree difference between actual and estimated eye orientation.

Non-idealities such as nonlinearities in the magnetic fields 228 of the coil 225 can introduce errors in the estimation of the eye orientation. Additional non-idealities may include differences in windings of the coils or areas enclosed by the coils. By use of the field divergence model, non-idealities above can be accounted for and errors in the estimation of the eye orientation can be reduced.

The eye tracking module 440 interoperates with the scleral eye tracking system 420 and the scleral lens 425 for performing scleral eye tracking. The eye tracking module 440 performs eye tracking based on the field divergence model. The eye tracking module 440 causes the scleral eye tracking system 420 to generate magnetic fields as described above. Moreover, the eye tracking module 440 receives electric signals from the scleral lens 425 in response to the magnetic fields generated from the scleral eye tracking system 420. The eye tracking module 440 analyzes the electric signals to determine an orientation of an eye based in part of the field divergence model. In one embodiment, the eye tracking module 440 provides an image of a virtual reality or an augmented reality to the display headset 405 and performs eye tracking, while the image is presented at the display headset 405.

Advantageously, by performing calibration of the eye orientation to generate a field divergence model and performing eye tracking based on the field divergence model, accuracy of the prediction of the eye orientation improves. Accordingly, the scleral eye tracking system 100 can be implemented as a wearable system in a portable form factor including only a pair of coils in a Helmholtz configuration and an additional coil offset from the pair of coils. The accuracy and speed of the scleral tracking system 100 makes it useful as a benchmark that other eye tracking systems can be compared against.

Figure 5:
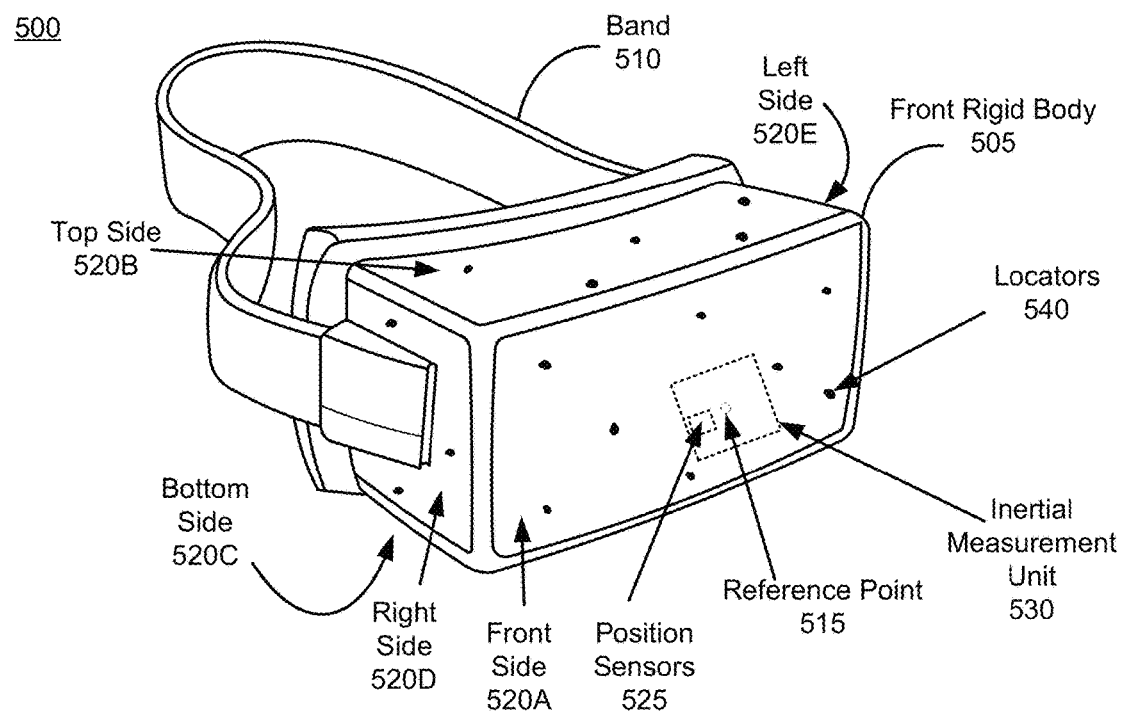
FIG. 5 is a diagram of a display headset, in accordance with an embodiment.

FIG. 5 is a diagram of the display headset 500, in accordance with an embodiment. The display headset 500 is an embodiment of the display headset 106 of FIG. 1A, and includes a front rigid body 505 and a band 510. In one embodiment, the band 510 may be e.g., the band 118 of FIG. 1B. In some embodiments, the display headset 500 is the display headset 405. The front rigid body 505 is configured to be situated in front of user eyes, and the band 510 is configured to be stretched and secure the front rigid body 505 on the user head in front of the user eyes.

In one embodiment, the front rigid body 505 is an apparatus on which an image is presented to a user. In the embodiment shown in FIG. 5, the front rigid body 505 includes a front side 520A, a top side 520B, a bottom side 520C, a right side 520D, and a left side 520E. An electronic display (not shown) is placed near the front rigid body 505, and the remaining sides (e.g., the top side 520B, bottom side 520C, right side 520D and left side 520E) ensure enough distance between the electronic display and eyes of the user for proper presentation of the image. In one embodiment, the sides 520 of the front rigid body 505 are opaque, such that a user wearing the display headset 500 cannot see outside of the display headset 500. In another embodiment, one or more of the sides 520 may be transparent.

In some embodiments, the display headset 500 further includes one or more locators 540, position sensors 525, and an inertial measurement unit (IMU) 530. The one or more locators 540, the position sensors 525, and the IMU 530 can be employed to determine a position of the user and an orientation of the user head. According to the determined position of the user and the orientation of the user head, an image can be displayed on the display headset 500 can be updated. Accordingly, a user can experience an immersive VR or AR experience.

The locators 540 are objects located in specific positions on the display headset 500 relative to one another and relative to a specific reference point 515 on the display headset 500. In some embodiments, one or more locators 540 are located beneath an outer surface of the front rigid body 505 of the display headset 500, which is transparent to the wavelengths of light emitted or reflected by the locators 540 or is thin enough not to substantially attenuate the wavelengths of light emitted or reflected by the locators 540.

A locator 540 may be a light emitting diode (LED), a corner cube reflector, a reflective marker, a type of light source that contrasts with an environment in which the display headset 500 operates, or some combination thereof. In embodiments where the locators 540 are active (i.e., an LED or other type of light emitting device), the locators 540 may emit light in the visible band (~380 nm to 750 nm), in the infrared (IR) band (~750 nm to 1 mm), in the ultraviolet band (10 nm to 380 nm), some other portion of the electromagnetic spectrum, or some combination thereof. An external imaging device (not shown) can detect light emitted or reflected from one or more locators 540 and determine a position or an orientation of the display headset 500.

A position sensor 525 generates one or more measurement signals in response to motion of the display headset 500. The position sensor 525 can be placed, for example, on the front rigid body 505. Examples of position sensors 525 include: one or more accelerometers, one or more gyroscopes, one or more magnetometers, another suitable type of sensor that detects motion, a type of sensor used for error correction of the IMU 530, or some combination thereof. The position sensors 525 may be located external to the IMU 530, internal to the IMU 530, or some combination thereof.

Based on the one or more measurement signals from one or more position sensors 525, the IMU 530 generates a signal indicating an estimated position of the display headset 500 relative to an initial position of the display headset 500. For example, the position sensors 525 include multiple accelerometers to measure translational motion (forward/back, up/down, left/right) and multiple gyroscopes to measure rotational motion (e.g., pitch, yaw, roll). In some embodiments, the IMU 530 rapidly samples the measurement signals and calculates the estimated position of the display headset 500 from the sampled data. For example, the IMU 530 integrates the measurement signals received from the accelerometers over time to estimate a velocity vector and integrates the velocity vector over time to determine an estimated position of a reference point 515 on the display headset 500. Alternatively, the IMU 530 provides the sampled measurement signals to an external device (not shown in FIG. 5), which determines an estimated position of the display headset 500. The reference point 515 is a point that may be used to describe the position of the display headset 500. While the reference point 515 may generally be defined as a point in space; however, in practice the reference point 515 is defined as a point within the display headset 500 (e.g., a center of the IMU 530).

In one embodiment, the display headset 500 can be coupled to the eye tracking system 100 of FIG. 1A. In this embodiment, the display headset 500 can be coupled to the eye tracking system 100 through one or more docking mounts 108 as shown in FIG. 1B.

In another embodiment, the display headset 500 is integrated with the eye tracking system. In one aspect, the display headset 500 includes coils (not shown) similar to the coils 115A, 115B, and 125 of FIG. 1A, but with smaller dimensions. For example, a first coil corresponding to the coil 115A is coupled to the right side 520D, and a second coil corresponding to the coil 115B is coupled to the left side 520E, hence the first coil and the second coil form a Helmholtz configuration for generating uniform magnetic fields. A third coil corresponding to the coil 125 can be coupled to any one of the front side 520A, top side 520B, and bottom side 520C, for generating non-uniform (divergent) fields. Alternatively, the first coil is coupled to the top side 520B, and the second coil is coupled to the bottom side 520C, where the third coil is coupled to any one of the front side 520A, right side 520D, and left side 520E. In other embodiments, a plurality of additional coils can be provided on any one of the sides 520. The parallel coils in Helmholtz configuration generate uniform magnetic fields, while one or more additional coils generate non-uniform divergent magnetic fields, as described with respect to FIG. 2.

Beneficially, with the display headset 500 secured to the eye tracking system 100 of FIG. 1 or integrated with coils as described above, a user can move while wearing the display headset 500. Thus, an eye tracking can be performed without restricting the user movement, while presenting an image of a VR or an AR to the user. As a result, how a human vestibular-ocular system responds to the VR or AR can be analyzed.

Additional Configuration Information

The foregoing description of the embodiments of the disclosure has been presented for the purpose of illustration; it is not intended to be exhaustive or to limit the disclosure to the precise forms disclosed. Persons skilled in the relevant art can appreciate that many modifications and variations are possible in light of the above disclosure.

Some portions of this description describe the embodiments of the disclosure in terms of algorithms and symbolic representations of operations on information. These algorithmic descriptions and representations are commonly used by those skilled in the data processing arts to convey the substance of their work effectively to others skilled in the art. These operations, while described functionally, computationally, or logically, are understood to be implemented by computer programs or equivalent electrical circuits, microcode, or the like. Furthermore, it has also proven convenient at times, to refer to these arrangements of operations as modules, without loss of generality. The described operations and their associated modules may be embodied in software, firmware, hardware, or any combinations thereof.

Any of the steps, operations, or processes described herein may be performed or implemented with one or more hardware or software modules, alone or in combination with other devices. In one embodiment, a software module is implemented with a computer program product comprising a computer-readable medium containing computer program code, which can be executed by a computer processor for performing any or all of the steps, operations, or processes described.

Embodiments of the disclosure may also relate to an apparatus for performing the operations herein. This apparatus may be specially constructed for the required purposes, and/or it may comprise a general-purpose computing device selectively activated or reconfigured by a computer program stored in the computer. Such a computer program may be stored in a non transitory, tangible computer readable storage medium, or any type of media suitable for storing electronic instructions, which may be coupled to a computer system bus. Furthermore, any computing systems referred to in the specification may include a single processor or may be architectures employing multiple processor designs for increased computing capability.

Embodiments of the disclosure may also relate to a product that is produced by a computing process described herein. Such a product may comprise information resulting from a computing process, where the information is stored on a non transitory, tangible computer readable storage medium and may include any embodiment of a computer program product or other data combination described herein.

Finally, the language used in the specification has been principally selected for readability and instructional purposes, and it may not have been selected to delineate or circumscribe the inventive subject matter. It is therefore intended that the scope of the disclosure be limited not by this detailed description, but rather by any claims that issue on an application based hereon. Accordingly, the disclosure of the embodiments is intended to be illustrative, but not limiting, of the scope of the disclosure, which is set forth in the following claims.

What is claimed is:

1. An eye tracking system comprising:
a first body enclosing a first area;
a second body enclosing a second area parallel to the first area, the second area facing the first area in a first direction;
an auxiliary body coupled to the first body and enclosing a third area, the third area facing the first area in a second direction offset from the first direction;
a first looping coil coupled to a perimeter of the first body;
a second looping coil coupled to a perimeter of the second body, the first looping coil and the second looping coil configured to generate substantially uniform magnetic fields; and
an auxiliary looping coil coupled to a perimeter of the auxiliary body, the auxiliary looping coil configured to generate divergent magnetic fields; and
a scleral lens configured to be worn on an eye of a user, the scleral lens placed within the substantially uniform magnetic fields and the divergent magnetic fields, the scleral lens including a scleral coil, the substantially uniform magnetic fields and the divergent magnetic fields inducing currents in the scleral coil that are used to determine an orientation of the eye.

2. The eye tracking system of claim 1, wherein the scleral coil is a torsional coil comprising two half loops configured to be situated proximate to a sclera of the eye.

3. The eye tracking system of claim 1,
wherein the first looping coil and the second looping coil are applied with an AC signal at a first frequency, and
wherein the auxiliary looping coil is applied with another AC signal at a second frequency different from the first frequency.

4. The eye tracking system of claim 1, further comprising:
a first bar coupled to the first body within the first area;
a second bar coupled to the second body within the second area; and
a docking mount coupled to the first bar at a center of the first area and coupled to the second bar at a center of the second area, the docking mount configured to be attached to a head-mounted display.

5. The eye tracking system of claim 4,
wherein the first area of the first body faces a first ear of the user wearing the head-mounted display attached to the docking mount,
wherein the second area of the second body faces a second ear of the user wearing the head-mounted display attached to the docking mount, and
wherein the third area of the auxiliary body away from the center of the first area faces the eye.

6. The eye tracking system of claim 1, further comprising:
a connector configured to mechanically couple the auxiliary body to the first body, the connector configured to change an orientation of the auxiliary body with respect to the first body.

7. The eye tracking system of claim 1, wherein the first body, the second body, and the auxiliary body have cylindrical shapes.

8. A system comprising:
an eye tracking system including:

a first body enclosing a first area, a second body enclosing a second area parallel to the first area, the second area facing the first area in a first direction, an auxiliary body coupled to the first body and enclosing a third area, the third area facing the first area in a second direction offset from the first direction;

a first looping coil coupled to a perimeter of the first body, a second looping coil coupled to a perimeter of the second body, the first looping coil and the second looping coil configured to generate substantially uniform magnetic fields, an auxiliary looping coil coupled to a perimeter of the auxiliary body, the auxiliary looping coil configured to generate divergent magnetic fields, and a scleral lens configured to be worn on an eye of a user, the scleral lens placed within the substantially uniform magnetic fields and the divergent magnetic fields, the scleral lens including a scleral coil, the substantially uniform magnetic fields and the divergent magnetic fields inducing currents in the scleral coil; and a console electrically coupled to the scleral lens, the console configured to receive electrical signals corresponding to the induced currents, the console further configured to determine an orientation of the scleral lens based on the electric signals received, the orientation of the scleral lens corresponding to an orientation of the eye.

9. The system of claim 8, wherein the console is configured to apply an AC signal at a first frequency to the first looping coil and the second looping coil, and apply another AC signal at a second frequency different from the first frequency to the auxiliary looping coil.

10. The system of claim 9, wherein the scleral coil is a torsional coil comprising two half loops configured to be situated proximate to a sclera of the eye, the two half loops comprising a first half loop and a second half loop.

11. The system of claim 10, wherein the console is further configured to perform frequency filtering on the electric signals to obtain four measurements from the electric signals, the four measurements comprising:

a first measurement at the first frequency corresponding to the substantially uniform magnetic fields through the first half loop;

a second measurement at the first frequency corresponding to the substantially uniform magnetic fields through the second half loop;

a third measurement at the second frequency corresponding to the divergent magnetic fields through the first half loop; and a fourth measurement at the second frequency corresponding to the divergent magnetic fields through the second half loop.

12. The system of claim 11, wherein the console is configured to determine the orientation of the scleral lens based on the four measurements.

13. The system of claim 8, further comprising:

a first bar coupled to the first body within the first area;

a second bar coupled to the second body within the second area; and a docking mount coupled to the first bar at a center of the first area and coupled to the second bar at a center of the second area, the docking mount configured to be attached to a head-mounted display.

14. The system of claim 13, wherein the first area of the first body faces a first ear of the user wearing the head-mounted display attached to the docking mount, wherein the second area of the second body faces a second ear of the user wearing the head-mounted display attached to the docking mount, and wherein the third area of the auxiliary body away from the center of the first area faces the eye of the user.

15. The system of claim 8, further comprising:

a connector configured to mechanically couple the auxiliary body to the first body, the connector configured to change an orientation of the auxiliary body with respect to the first body.

16. The system of claim 8, wherein the first body, the second body, and the auxiliary body have cylindrical shapes.

17. An eye tracking system comprising:

a first body enclosing a first area, a perimeter of the first body coupled to a first looping coil;

a second body enclosing a second area parallel to the first area, the second area facing the first area in a first direction, a perimeter of the second body coupled to a second looping coil, the first looping coil and the second looping coil configured to generate substantially uniform magnetic fields;

an auxiliary body coupled to the first body and enclosing a third area, the third area facing the first area in a second direction offset from the first direction, a perimeter of the auxiliary body coupled to an auxiliary looping coil, the auxiliary looping coil configured to generate divergent magnetic fields; and a scleral lens configured to be worn on an eye of a user, the scleral lens placed within the substantially uniform magnetic fields and the divergent magnetic fields, the scleral lens including a scleral coil, the substantially uniform magnetic fields and the divergent magnetic fields inducing currents in the scleral coil that are used to determine an orientation of the eye.

18. The eye tracking system of claim 17, wherein the scleral coil is a torsional coil comprising two half loops configured to be situated proximate to a sclera of the eye.

19. The eye tracking system of claim 17, wherein the first looping coil and the second looping coil are applied with an AC signal at a first frequency, and wherein the auxiliary looping coil is applied with another AC signal at a second frequency different from the first frequency.

20. The eye tracking system of claim 17, wherein the first area of the first body faces a first ear of the user wearing a head-mounted display coupled to the eye tracking system, wherein the second area of the second body faces a second ear of the user wearing the head-mounted display coupled to the eye tracking system, and wherein the third area of the auxiliary body away from a center of the first area faces the eye.

* * * * *